(12) United States Patent
Huang et al.

(10) Patent No.: US 7,019,453 B2
(45) Date of Patent: Mar. 28, 2006

(54) POLYMERS HAVING PENDANT NONLINEAR OPTICAL CHROMOPHORES AND ELECTRO-OPTIC DEVICES THEREFROM

(75) Inventors: Diyun Huang, Bothell, WA (US); Baoquan Chen, Bothell, WA (US)

(73) Assignee: Lumera Corporation, Bothell, WA (US)

( * ) Notice: Subject to any disclaimer, the term of this patent is extended or adjusted under 35 U.S.C. 154(b) by 302 days.

(21) Appl. No.: 10/625,371

(22) Filed: Jul. 23, 2003

(65) Prior Publication Data

US 2004/0132960 A1 Jul. 8, 2004

Related U.S. Application Data

(63) Continuation-in-part of application No. 10/395,610, filed on Mar. 24, 2003, which is a continuation of application No. 10/301,978, filed on Nov. 22, 2002, now Pat. No. 6,750,603, which is a continuation-in-part of application No. 09/932,831, filed on Aug. 17, 2001, now Pat. No. 6,716,995.

(60) Provisional application No. 60/226,267, filed on Aug. 17, 2000.

(51) Int. Cl.
*H01J 1/62* (2006.01)
*G02B 26/00* (2006.01)

(52) U.S. Cl. ............ 313/483; 359/326; 359/237; 385/2; 385/122; 385/141; 430/630

(58) Field of Classification Search .......... 313/483; 359/326, 237; 385/2, 122, 141; 430/630
See application file for complete search history.

(56) References Cited

U.S. PATENT DOCUMENTS

| | | | |
|---|---|---|---|
| 4,028,702 A | 6/1977 | Levine | |
| 4,258,386 A | 3/1981 | Cheung | |
| 5,041,516 A | 8/1991 | Frechet et al. | |
| 5,051,754 A | 9/1991 | Newberg | |
| 5,198,513 A | 3/1993 | Clement et al. | |
| 5,207,952 A | 5/1993 | Griffin, III | |
| 5,223,356 A | 6/1993 | Kumar et al. | |
| 5,266,365 A | 11/1993 | Kester et al. | |
| 5,353,033 A | 10/1994 | Newberg et al. | |
| 5,359,008 A | 10/1994 | Amano et al. | |
| 5,395,556 A | 3/1995 | Drost et al. | |
| 5,433,895 A | 7/1995 | Jeng et al. | |
| 5,520,968 A | 5/1996 | Wynne et al. | |
| 5,635,576 A | 6/1997 | Foll et al. | |
| 5,670,091 A | 9/1997 | Marder et al. | |
| 5,679,763 A | 10/1997 | Jen et al. | |
| 5,696,243 A | 12/1997 | Beckmann et al. | |
| 5,714,304 A | 2/1998 | Gibbons et al. | |
| 5,776,374 A | 7/1998 | Newsham et al. | |
| 5,783,649 A | 7/1998 | Beckmann et al. | |
| 5,811,507 A | 9/1998 | Chan et al. | |
| 5,861,976 A | 1/1999 | Hoekstra | |
| 6,067,186 A | 5/2000 | Dalton et al. | |
| 6,090,332 A | 7/2000 | Marder et al. | |
| 6,126,867 A | 10/2000 | Kanitz et al. | |
| 6,130,339 A | 10/2000 | Tan et al. | |
| 6,197,921 B1 | 3/2001 | Tan et al. | |
| 6,228,977 B1 | 5/2001 | Kanitz et al. | |
| 6,294,573 B1 | 9/2001 | Curtin et al. | |
| 6,716,995 B1 * | 4/2004 | Huang et al. | 549/62 |
| 6,750,603 B1 * | 6/2004 | Huang et al. | 313/483 |

FOREIGN PATENT DOCUMENTS

| | | |
|---|---|---|
| DE | 4401911 | 8/1995 |
| DE | 4416476 | 11/1995 |
| DE | 19532828 | 3/1996 |
| EP | 0414185 | 2/1991 |
| EP | 0637774 | 2/1995 |
| EP | 0729056 | 2/1995 |
| EP | 0754709 | 1/1997 |
| JP | 08108624 | 4/1996 |
| JP | 200089268 | 3/2000 |
| JP | 2001085713 | 3/2001 |

OTHER PUBLICATIONS

March, "Classification of Reactions by Type of Compound Synthesized", *Advanced Organic Chemistry Reactions, Mechanisms, and Structure*, 1992, 4th Edition, John Wiley & Sons, New York, pp. 1269-1300.

Chen et al., "Thermosetting Polyurethanes with Stable and Large Second-Order Optical Nonlinearity", *Macromolecules*, 1992, 25(15):4032-4035.

Gorman et al., "An Investigation of the Interrelationships Between Linear and Nonlinear Polarizabilities and Bond-Length Alternation in Conjugated Organic Molecules", *Proc. Natl. Acad. Sci. USA*, 1993, 90(23):11297-11301.

Smith et al, "Perfluorocyclobutane Aromatic Polyethers. Synthesis and Characterization of New Siloxane-Containing Fluoropolymers", *Macromolecules*, 1996, 29(3):852-860.

(Continued)

*Primary Examiner*—Deborah C. Lambkin
(74) *Attorney, Agent, or Firm*—Fish & Richardson, P.C., P.A.

(57) ABSTRACT

A nonlinear optical chromophore having the formula D-π-A, wherein π is a π bridge including a thiophene ring having oxygen atoms bonded directly to the 3 and 4 positions of the thiophene ring, D is a donor, and A is an acceptor.

19 Claims, 12 Drawing Sheets

OTHER PUBLICATIONS

Kojima et al., "Facile Synthesis of Thiophene Derivatives Using a Cyclopropenyl Cation", *Synthesis*, 1996, 10:1193-1195.

Landmesser et al. "Regiocontrolled C-8 Acylation of Castanospermine", *Synthetic Comm.*, 1996, 26(11):2213-2221.

Mao et al., "Progress Toward Device-Quality Second-Order Nonlinear Optical Materials. 1. Influence of Composition and Processing Conditions on Nonlinearity, Temporal Stability, and Optical Loss", *Chem. Mater.*, 1998, 10(1): 146-155.

Reinhart et al., "Highly Active Two-Photon Dyes: Dessign, Synthesis, and Characterization Toward Application", *Chem. Mater.*, 1998, 10:1863-1874.

Bosman et al., "About Dendrimers: Structure, Physical Properties, and Applications", *Chem. Rev.*, 1999, 9(7):1665-1688.

Ma et al., "A Convenient Modular Approach of Functionalizing Aromatic Polyquinolines for Electrooptic Devices", *Chem. Mater.*, 1999, 11(8):2218-2225.

Kim et al., "Nonlinear Optical Chromophores Containing Dithienothiophene as a New Type of Electron Relay", *J. Mater. Chem.*, 1999, 9:2227-2232.

Ma et al., "A Novel Class of High-Performance Perfluorocyclobutane-Containing Polymers for Second-Order Nonlinear Optics",*Chem. Mater*, 2000, 12(5):1187-1189.

Ma et al., "Highly Efficient and Thermally Stable Nonlinear Optical Dendrimer for Electrooptics", *J. Am. Chem. Soc.*, 2001, 123(5):986-987.

Raimundo et al. "Push-Pull Chromophores Based on 2,2'-Bi(3,4-ethylenedioxythiophene) (BEDOT) π-Conjugating Spacer" *Tetrahedron Letters*, 2001, 42:1507-1510.

Luo et al., "Design, Synthesis, and Properties of Highly Efficient Side-Chain Dendronized Nonlinear Optical Polymers for Electro-Optics", *Adv. Mater.*, 2002, 14(23): 1763-1768.

Liu et al., "Focused Microwave-Assisted Synthesis of 2,5-Dihydrofuran Derivatives as Electron Acceptors for Highly Efficient Nonlinear Optical Chromophores", *Adv. Mater.*, 2003, 15(7-8):603-607.

* cited by examiner

Bz

Dn

31: R = Bz
35: R = Dn

36: R = Bz
37: R = Dn

POLYMERS HAVING PENDANT NONLINEAR OPTICAL CHROMOPHORES AND ELECTRO-OPTIC DEVICES THEREFROM

RELATED APPLICATIONS

This application is a continuation-in-part of patent application Ser. No. 10/395,610 filed Mar. 24, 2003, which is a continuation of Ser. No. 10/301,978 filed Nov. 22, 2002 now U.S. Pat. No. 6,750,603, which is a continuation-in-part of patent application Ser. No. 09/932,831 filed Aug. 17, 2001 now U.S. Pat. No. 6,716,995, entitled "Design and Synthesis of Advanced NLO Materials for Electro-Optic Applications," which is assigned to the same assignee as the present application, which claims benefit of Provisional Application No. 60/226,267 filed Aug. 17, 2000, and which is hereby incorporated by reference in its entirety.

All patents, patent applications, and publications cited within this application are incorporated herein by reference to the same extent as if each individual patent, patent application or publication was specifically and individually incorporated by reference.

BACKGROUND OF THE INVENTION

The invention relates generally to the organic chromophores for second order nonlinear optical (NLO) applications, compositions including such chromophores, and applications including such chromophores and compositions.

The development and uses of NLO chromophores, including polymer matrix development, waveguide fabrication, and optical device fabrication are well documented. An NLO chromophore (also known as a "push-pull" chromophore) comprises three fundamental building blocks represented by the general formula D-π-A, where D is a donor, π is a π-bridge, and A is an acceptor. In the art, a "π-bridge" is sometimes referred to as a "π-conjugated bridge," "π-electron bridge," "conjugated π-electron bridge," and the like. Examples of such bridges are described, for example, in U.S. Pat. Nos. 5,670,091, 5,679,763, 6,067,186, and 6,090,332. A "π-bridge" allows charge transfer from a donor to an acceptor in a chromophore. Exemplary acceptors are shown in FIG. 1, where, independently at each occurrence, $R^1$ is hydrogen, a halogen except when bonded to a carbon alpha to or directly to a nitrogen, oxygen, or sulfur atom, or an alkyl, aryl, heteroalkyl, or heteroaryl group; Y is O, S or Se; and q is 0 or 1. Exemplary donors are shown in FIG. 2, where, independently at each occurrence, $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1. Herein, a heteroalkyl group includes, but is not limited to, functional groups, halogen substituted alkyl groups, perhalogenated alkyl groups, and dendrons. What is meant by a functional group in generally understood in the art of organic chemistry, for example see Appendix B in Jerry March, "Advanced Organic Chemistry" $4^{th}$ Edition, John Wiley and Sons, New York, pp 1269–1300. A "dendron" is a substituent that has regularly repeating subunits. A dendron may be further comprised of one or more heteroaryl group. A "dendrimer" is a macromolecular structure that contains a "core" surrounded by one or more dendrons. Often in the art, the terms dendron and dendrimer are used interchangeably. Dendrons and dendrimers are illustrated and discussed in Bosman et al., *Chem. Rev.* 1999, 99, 1665 and U.S. Pat. No. 5,041,516.

The particular D-π-A arrangement affects the ability of the molecule to achieve large second order NLO effects. Thus, the first molecular electronic hyperpolarizability (β, sometimes given as μβ, where μ is the dipole moment of the chromophore), which is a measure of this ability, can be tuned and optimized by changing the electronic properties of any one of D, π, or A, see Gorman and Marder *Proc. Natl. Acad. Sci, USA* 1993, 90, 11297. Molecular NLO effects, in turn, can be translated into bulk EO activity in a material by aligning molecules in one direction by applying an electric field.

SUMMARY OF THE INVENTION

In one aspect, a nonlinear optical chromophore has the formula D-π-A where π is a π bridge including a thiophene ring having oxygen atoms bonded directly to the 3 and 4 positions of the thiophene ring, D is a donor, and A is an acceptor. The oxygens bonded directly to the 3 and 4 ring positions of the of the thiophene ring may be further independently substituted with an alkyl group comprising 1 to about 20 carbons, a heteroalkyl group comprising 1 to about 20 carbons, an aryl group comprising 1 to about 20 carbons, or a heteroaryl group comprising 1 to about 20 carbons.

In a second aspect, a nonlinear optical chromophore has the formula:

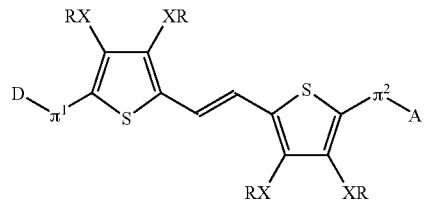

wherein, independently at each occurrence: $\pi^1$ is absent or a π-bridge; $\pi^2$ is absent or a π-bridge; D is an donor; A is an acceptor; X is O or S; and R is an alkyl group comprising 1 to about 20 carbons, a heteroalkyl group comprising 1 to about 20 carbons, an aryl group comprising 1 to about 20 carbons, or a heteroaryl group comprising 1 to about 20 carbons.

These chromophores may be combined with a polymer matrix to form second order nonlinear optical compositions useful in a variety of applications, including electro-optic devices such as optical modulators, optical switches, and optical directional couplers. For example, the chromophore and polymer matrix may contain crosslinkable functional groups, and may be combined to form a guest-host composite, in which the chromophore is the guest and the polymer matrix is the host. An electric field is then applied to the composite to induce electro-optic activity, after or during which the composite is crosslinked to covalently bond the chromophore to the polymer matrix.

In another embodiment, a linear polymer comprises pendant chromophores having the formula D-π-A, where π is a π bridge including a thiophene ring having oxygen atoms bonded directly to the 3 and 4 positions of the thiophene ring, D is a donor, and A is an acceptor, as described above. Preferably, the pendant chromophores have the formula:

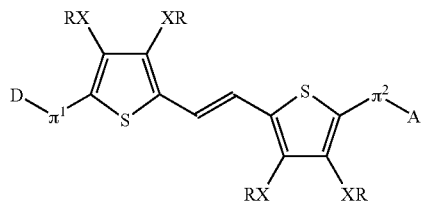

where the substituents are as defined above. The polymer may further include pendant crosslinkable groups and the chromophore may further included at least one crosslinkable group.

Other features and advantages of the invention will be apparent from the following description of preferred embodiments thereof, and from the claims.

DETAILED DESCRIPTION

Figure 1:
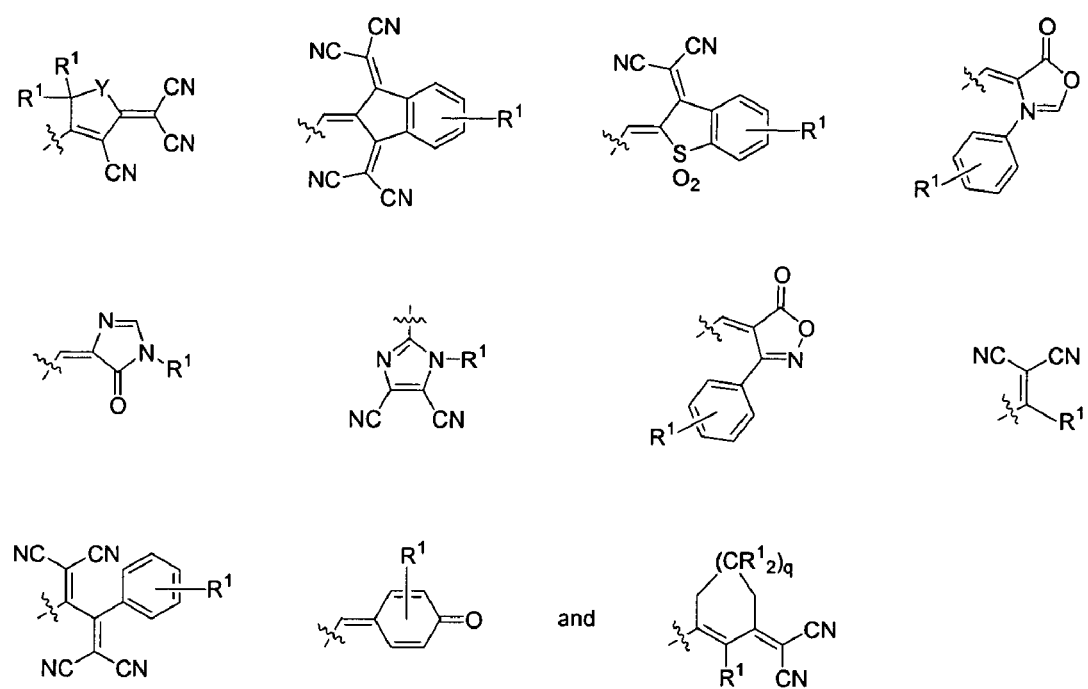
FIG. 1 illustrates exemplary acceptors that can be used in some embodiments.
Figure 2:
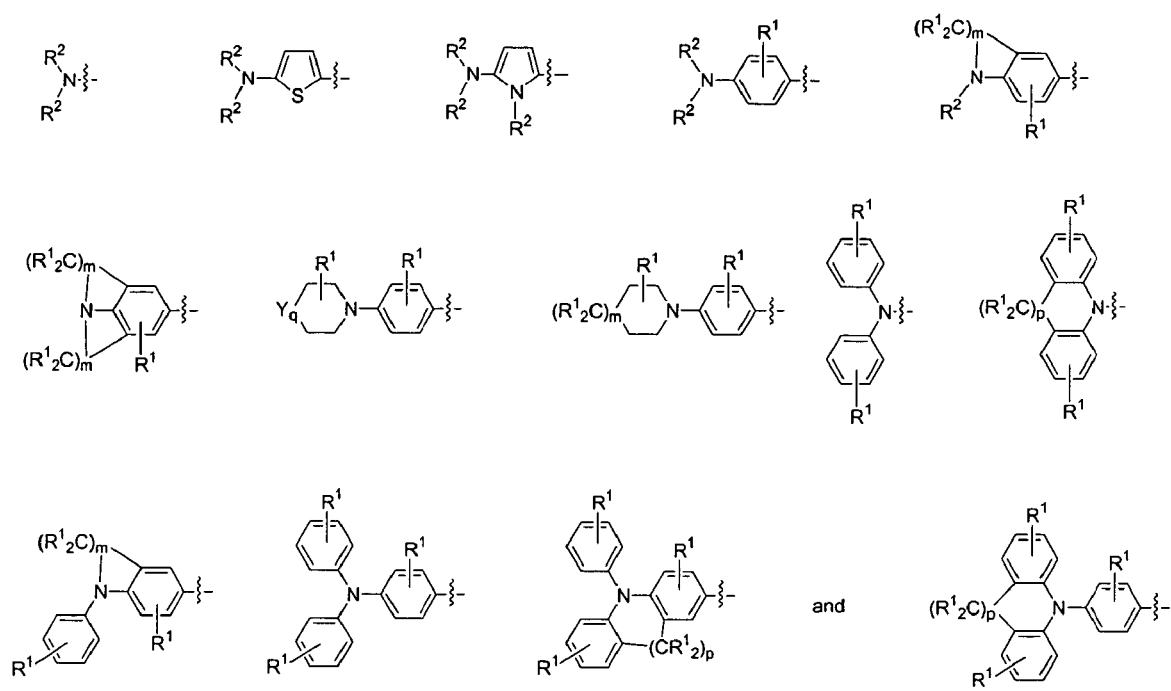
FIG. 2 illustrates exemplary donors that can be used in some embodiments.

The second order nonlinear optical chromophores have the chemical structures and formulas described above in the Summary of the Invention. Examples of donors (D) that may be used include structures chosen from the group consisting of

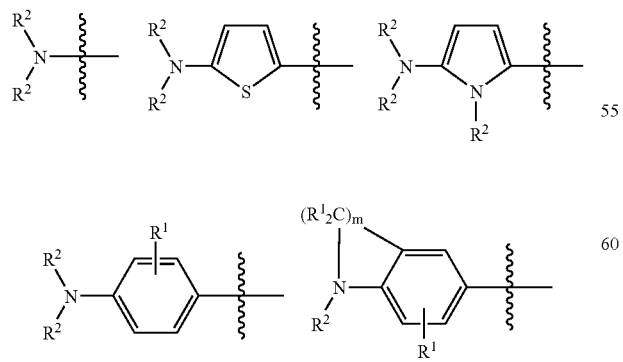

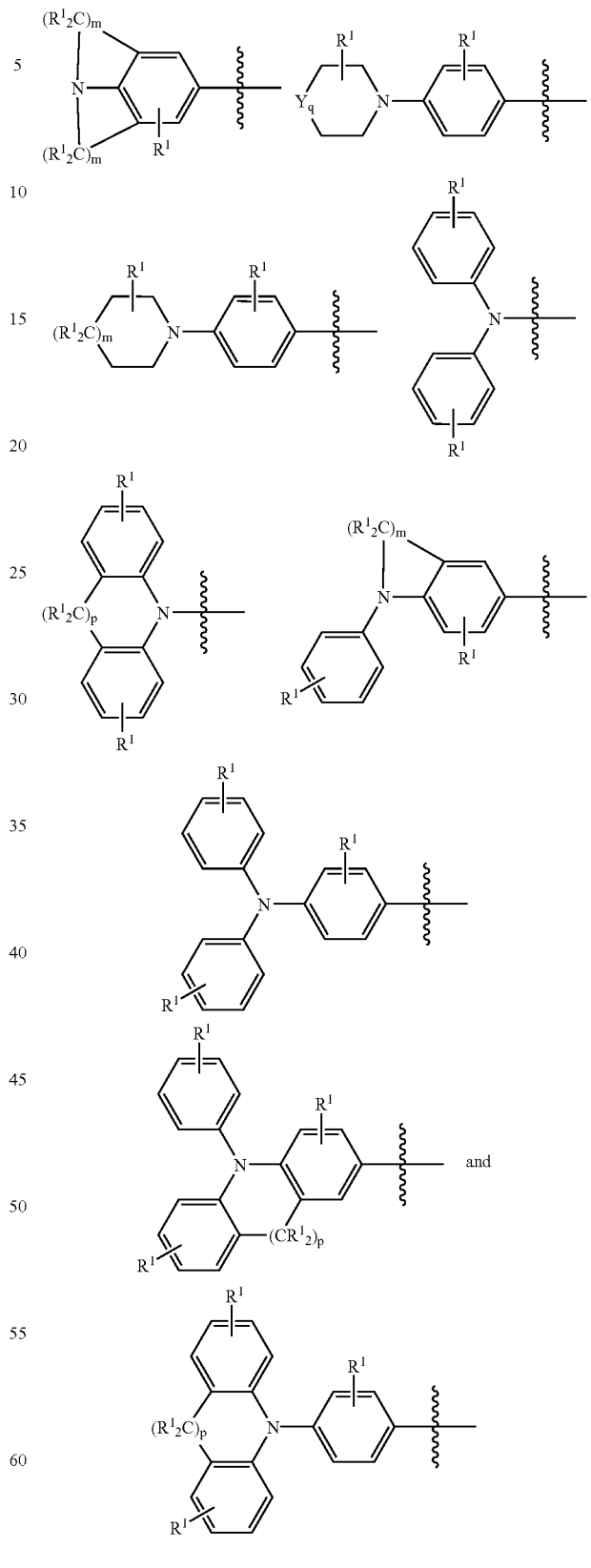

Examples of acceptors (A) that may be used include structures selected from the group consisting of

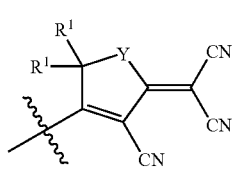 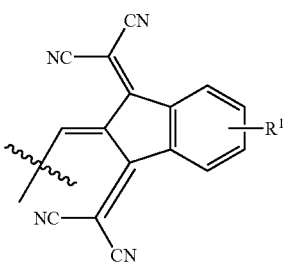 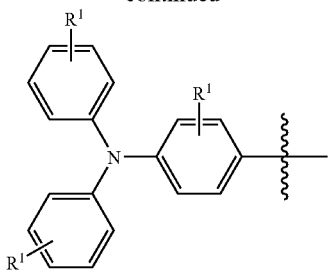

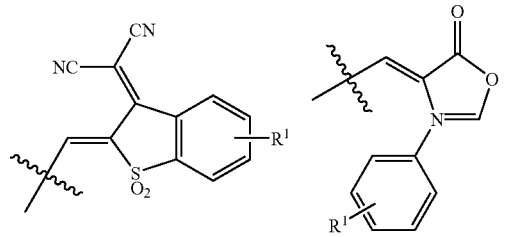

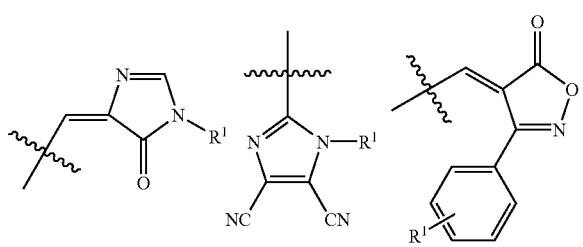

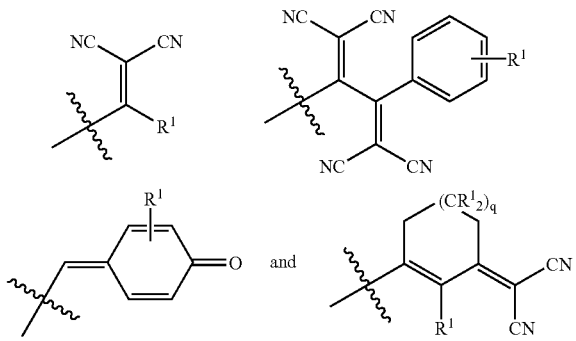

wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1. Preferably, the donor is chosen from the group consisting of wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; and $R^2$ is hydrogen or an alkyl, aryl, heteroalkyl, or heteroaryl group.

The chromophores may be combined with a polymer matrix to form compositions useful in a variety of electro-optical applications. Such compositions may be prepared according to a number of known techniques, including those described in U.S. Pat. Nos. 5,776,374; 5,714,304; 5,223,356; 5,433,895; 6,294,573; 6,126,867; 5,811,507; 5,635,576; 5,520,968; 5,359,008; 5,266,365; 5,207,952; and 6,228,977 and Chem. Mater. 2000, 12, 1187; J. Am Chem. Soc. 2001, 123, 986; Macromolecules 1992, 25, 4032; Chem. Mater. 1999, 11, 2218; and Chem. Mater. 1998, 10, 146. In one embodiment, the chromophore is a guest in the crosslinked polymer matrix host. In another embodiment, the chromophore is covalently incorporated into a crosslinked polymer matrix, the chromophore being at first a guest in a crosslinkable polymer matrix host. In yet another embodiment, the chromophore is covalently attached to a linear polymer as a pendant group.

Another embodiment is a process comprising: 1) providing a guest chromophore in a polymer host, wherein both the guest chromophore and polymer host contain fluorinated crosslinkable groups; 2) applying an electric field to the composite to induce electro-optic activity; and 3) crosslinking the composite, whereby the chromophore guest is covalently incorporated into the polymer host to provide a crosslinked nonlinear optical material. This method has advantages over other conventional processes, such as: 1) the chromophore guest and polymer host are compatible due to both having fluorinated crosslinkable groups; 2) the nonlinear optical material produced will have lower loss at 1550 nm since the crosslinking groups are fluorinated; 3) the chromophore host has more degrees of freedom to align with the poling field since it is not covalently incorporated into the polymer host before the poling filed is applied; and 4) the molecular weight and composition of the polymer are precisely known, which will allow control of critical parameters like film thickness, $T_g$, and solubility.

The nonlinear optical compositions may be used to fabricate optical devices, optical switches, modulators, waveguides, or other electro-optical devices that can be used in communication systems using methods known in the art. For example, in optical communication systems, devices fabricated including compositions described above may be incorporated into routers for optical communication systems, waveguides for optical communication systems, or for optical switching or computing applications. Because polymers are generally less demanding than currently used materials, devices including compositions described above may be more highly integrated.

Specific examples of components of optical communication systems that may be fabricated in whole or in part from the nonlinear optical compositions described above include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings.

Waveguides made with nonlinear optical compositions described above may be used in telecommunication, data communication, signal processing, information processing, and radar system devices and thus may be used in communication methods relying, at least in part, on the optical transmission of information. Specific applications in which the above-described nonlinear optical compositions can be incorporated include:

(1) an electro-optic device that is an interferometric optical modulator or switch, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one waveguide includes a nonlinear optical composition described above.

(2) an optical modulator or switch, comprising: 1) an input; 2) an output; 3) a first waveguide extending between the input and output; and 4) a second waveguide aligned to the first waveguide and positioned for evanescent coupling to the first waveguide; wherein at least one waveguide includes a nonlinear optical composition described above.

(3) an optical router that includes at least one optical modulator, optical switch, or optical directional coupler comprising a nonlinear optical composition described above.

Additional applications include a communications system including at least one electro-optic device comprising a nonlinear optical composition described above, a method of data transmission including transmitting light through a nonlinear optical composition described above, a method of telecommunication including transmitting light through a nonlinear optical composition described above, a method of transmitting light including directing light through or via a nonlinear optical composition described above, and a method of routing light through an optical system comprising transmitting light through or via a nonlinear optical composition described above.

Additionally, the nonlinear optical compositions described herein may be applied to devices or methods that control the phase of light waves passing through the material. In some applications, electrical fields are applied across a set of waveguides through which the light waves travel. Controlling the electrical fields allows the relative phases of the light waves to be controlled. Such approaches are particularly useful in applications known in the art such as phased-array radar or phase matching of light waves passing through alternative waveguides, for example see, U.S. Pat. Nos. 5,353,033; 5,051,754; 4,258,386; and 4,028,702. Thus, another embodiment is a phased-array radar comprising a nonlinear optical composition embodiment described above.

The following examples are illustrative and are not intended as a limitation thereof.

EXAMPLES

Example 1

Figure 3:
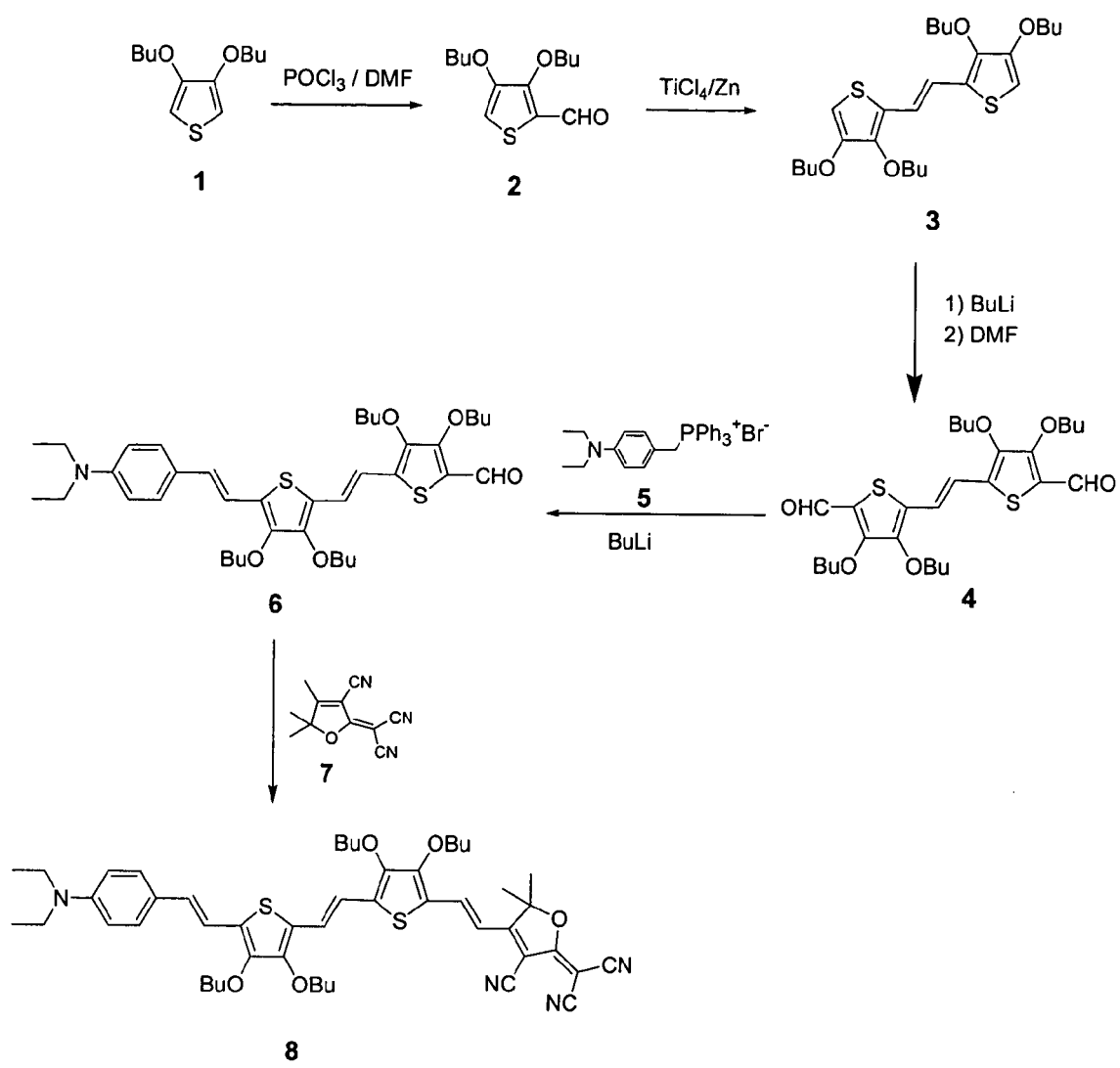
FIGS. 3–6 outline syntheses of various nonlinear optical chromophores.

Referring to FIG. 3, Compound 1, which was prepared as in *Syn. Comm.* 1996, 26, 2213, (187.8 g, 0.824 mol), dry DMF (127.4 mL, 1.647 mol) and dry dichloromethane (2000 mL) were mixed in a 3-neck flask and cooled to 0° C. $POCl_3$ (201.6 g, 1.318 mol) was added. The mixture was heated to reflux for 3 h. Then it was poured into 1 M NaOAc solution. It was extracted with $CH_2Cl_2$, washed with water and dried over $MgSO_4$. After removing the solvent, it was purified by flash column with ethyl acetate/hexane (1:2.5) to give 200 g (95%) of Compound 2.

Zinc (61.5 g, 0.941 mol) and dry THF (950 mL) were placed in a 3-neck flask and cooled to 0° C. $TiCl_4$ (51.5 mL, 0.469 mol) was added slowly. The mixture was then heated to reflux for half hour. It was then cooled to 0° C. A solution of compound 2 (60 g, 0.234 mol) and pyridine (49.5 mL, 0.605 mol) in THF (200 mL) was added slowly. The mixture was heated to reflux for 2 h. After cooling to room temperature, ice and $CH_2Cl_2$ were added. The resulting mixture was filtered through zelite, washed with HCl solution, water and dried over $MgSO_4$. After removing the solvent, the crude solid was purified by recrystallization from methanol to give 42.4 g (75%) of Compound 3.

Compound 3 (75 g, 0.156 mol) and ether (1400 mL) were placed in a flask and cooled to 0° C. BuLi (2.5 M) (156 mL, 0.39 mol) was added slowly and stirred for 15 min. DMF (57 mL, 0.733 mol) was then added, after which the mixture was warmed to room temperautre and stirred. $NH_4Cl$ solution was added and the solvent was partially removed under reduced pressure. It was then extracted with $CH_2Cl_2$, washed with water, and dried over $MgSO_4$. After removing the solvent, the crude product was purified by recrystallization from methanol to give 76 g (91%) of Compound 4.

Compound 5 (2.74 g, 5.44 mmol) and THF (200 mL) were mixed and stirred. At −40° C., BuLi (2.5 M) (2.4 mL, 5.98 mmol) was added and then stirred at room temperature for 30 min. The resulting solution was added slowly to a solution of Compound 4 (2.65 g, 4.94 mmol) in 100 mL THF with stirring. The solution was stirred at room temperature for 8 h, after which the solvent was removed at reduced pressure. The remaining crude material was purified by column chromatography with hexane/$CH_2Cl_2$/ethyl acetate mixture to give 2.65 g (76%) of Compound 6 (which may have a slight impurity of di-reacted product).

Compound 6 (2.65 g, 3.9 mmol), Compound 7 (1.55 g, 7.8 mmol), $CHCl_3$ (2 mL), and piperidine (2 drops) were mixed and refluxed for 3 h. The reaction was monitored with thin layer chromatography until the bulk color changed to dark blue/green. The product was purified by flash column and regular column chromatography with $CH_2Cl_2$/ethyl acetate/ hexane mixture to give 1.5 g (45%) of Compound 8.

An electro-optic polymer thin film including chromophore Compound 8 was prepared by: 1) obtaining a solution of Compound 8 and poly [biphenyl A carbonate-co-4,4'-(3,3,5-trimethylcyclohexylidene)-diphenol carbonate] from Aldrich (27% by weight loading of Compound 8 with respect to the polycarbonate) in dibromomethane (6.67% by weight loading of the dibromomethane with respect to Compound 8 and the polycarbonate); 2) spin depositing the solution at 500 rpm for 5 sec and 1500 rpm for 30 sec on a 2" diameter indium tin oxide (ITO) substrate; 3) sputtering a gold electrode on the polymer thin film; and 4) poling at 124° C. for 5–10 min in silicon oil with a poling voltage of 100–150 V/μm.

Example 2

Figure 4:
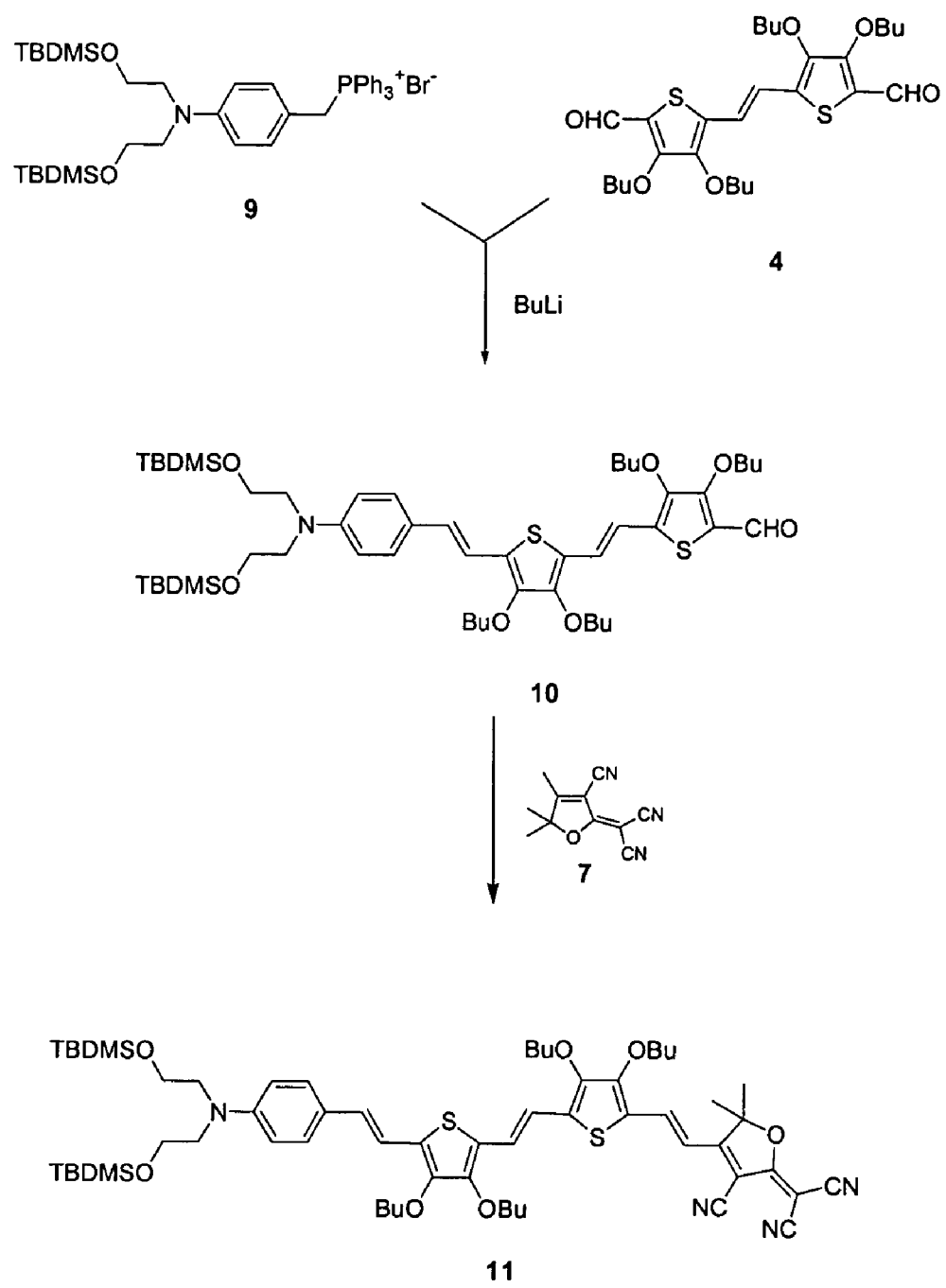
Figure 5:
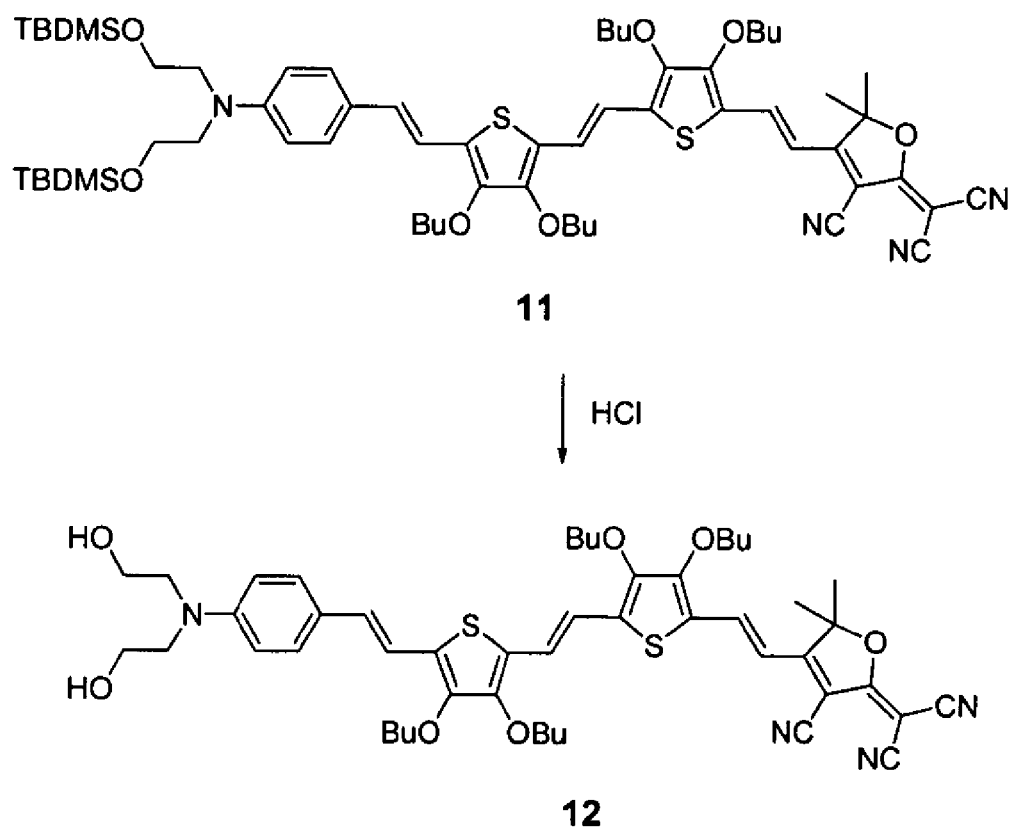
Figure 6:
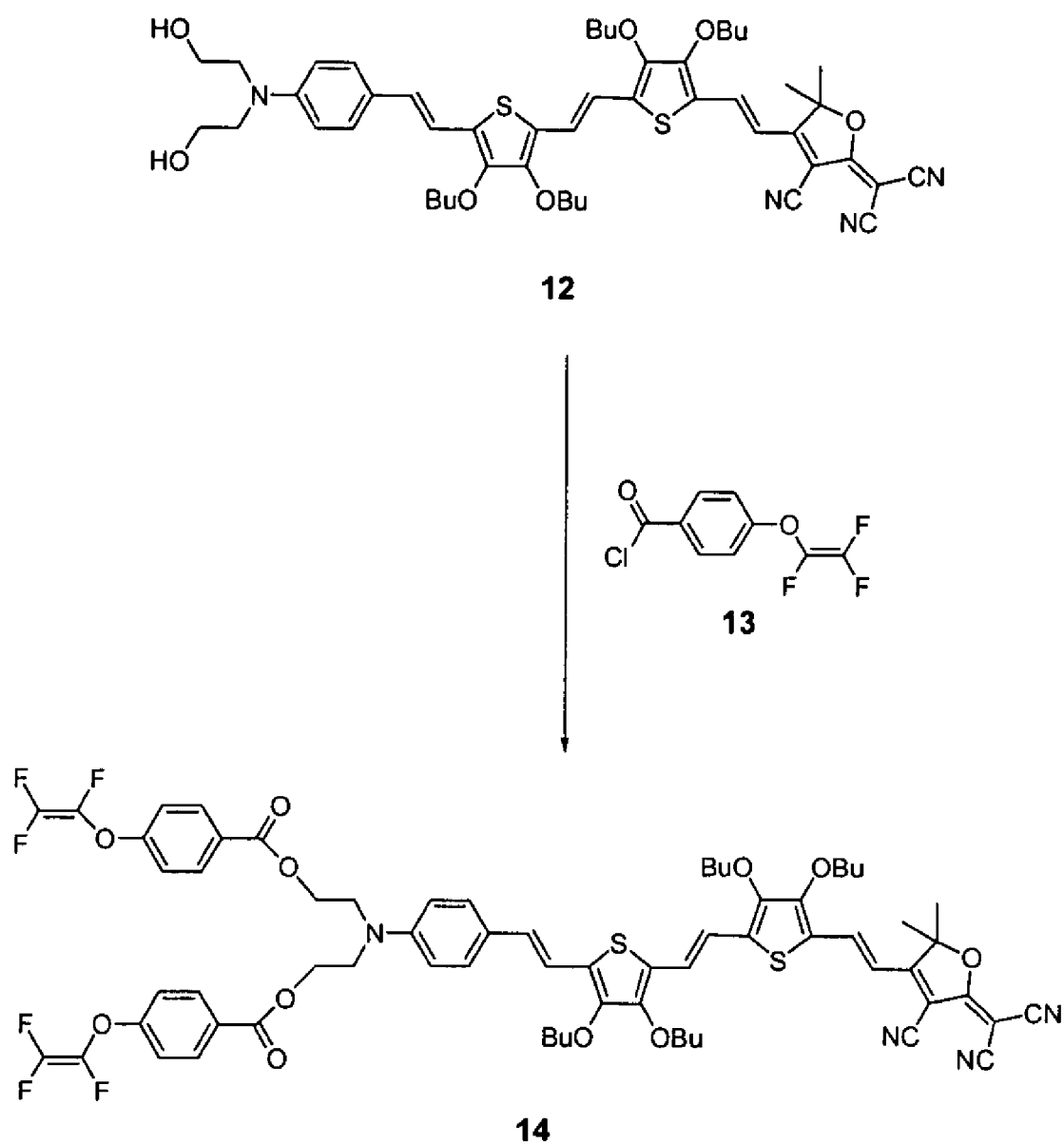

Referring to FIGS. 4–6, Compound 9 (82 g, 0.107 mol) and THF (2500 mL) were mixed and stirred. At −40° C., BuLi (2.5 M) (47.4 mL, 0.118 mol) was added and then stirred at room temperature for 30 min. The resulting solution was added slowly to a solution of Compound 4 (50 g, 0.093 mol) dissolved in 1500 mL THF. The resulting solution was then stirred at room temperature for 8 h. The solvent was removed at reduced pressure. The remaining crude material was purified by column chromatography with hexane/$CH_2Cl_2$/ethyl acetate mixture to give 61.3 g (70%) of Compound 10.

Compound 10 (61 g, 0.065 mol), Compound 7 (26 g, 0.129 mol), $CHCl_3$ (20 mL) and piperidine (10 drops) were mixed and refluxed for 3 h. The reaction was monitored with thin layer chromatography until the bulk color changed to dark blue/green. The product was purified by flash column and regular column chromatography with $CH_2Cl_2$/ethyl acetate/hexane mixture to give 36 g (49%) of Compound 11.

Compound 11 was dissolved in 750 mL THF. HCl solution (1 N, 250 mL) was added and the resulting solution was stirred for 8 h. After checking the reaction with thin layer chromatography, $NaHCO_3$ solution was added. The resulting solution was then extracted with $CH_2Cl_2$, washed with water, and dried over $MgSO_4$. After removing the solvent under reduced pressure, the remaining material was purified by flash column chromatography with $CH_2Cl_2$/ethyl acetate mixture to give 17.8 g (63%) of Compound 12.

Compound 13, which can be prepared as in U.S. Pat. No. 5,198,513 or by carbonylation of the lithium salt of Compound 15 (FIG. 7) followed by reaction with thionyl chloride, (23.5 g, 0.099 mol) was dissolved in 50 mL $CH_2Cl_2$ and cooled to 0° C. Compound 12 (17.8 g, 0.0199 mol) and pyridine (9.6 mL, 0.119 mol) were dissolved in 200 mL $CH_2Cl_2$ and added slowly to the solution of Compound 13. The resulting solution was stirred at room temperature for 8 h. The mixture was then extracted with $CH_2Cl_2$, washed with water, and dried over $MgSO_4$. After removing the solvent under reduced pressure, the remaining material was purified by flash column chromatography with $CH_2Cl_2$/ethyl acetate mixture to give 21 g (83%) of Compound 14.

Figure 7:
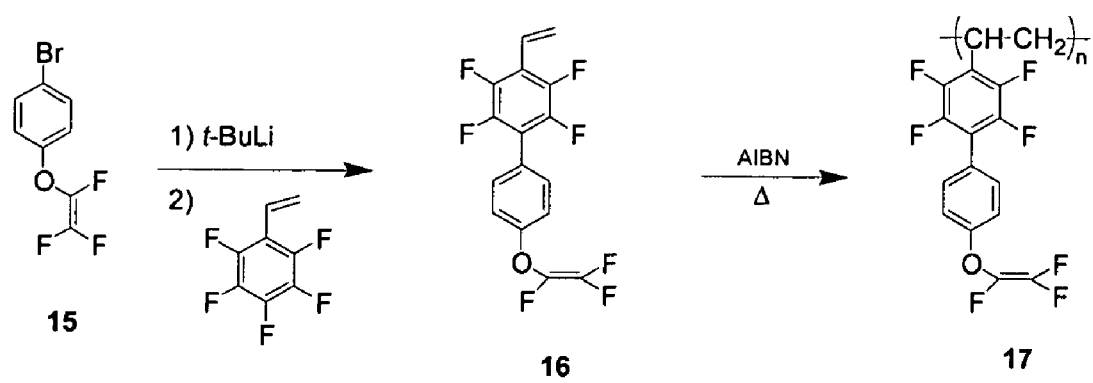
FIG. 7 outlines a synthesis of a crosslinkable polymer used in some embodiments.
Figure 8:
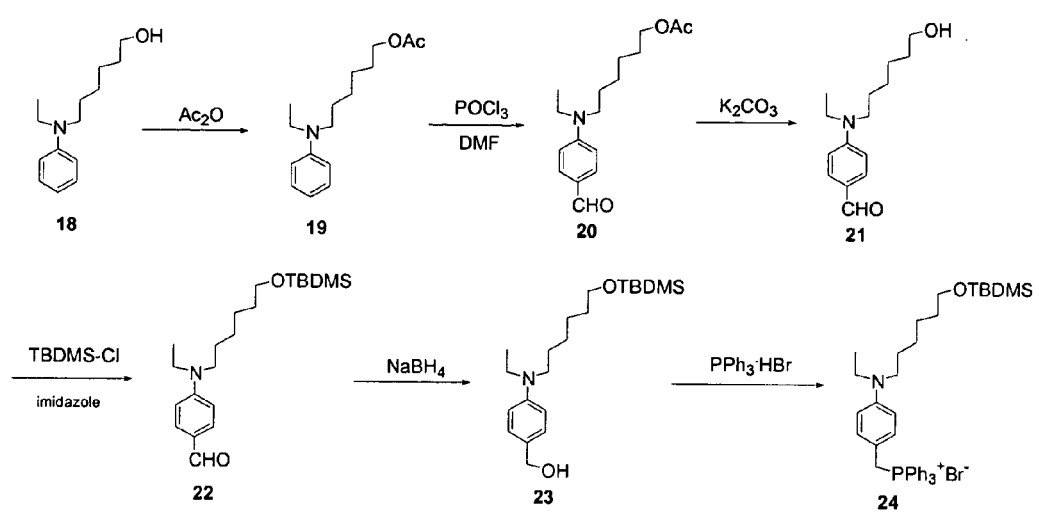
FIGS. 8-10 outline the syntheses of nonlinear optical chromophores.
Figure 9:
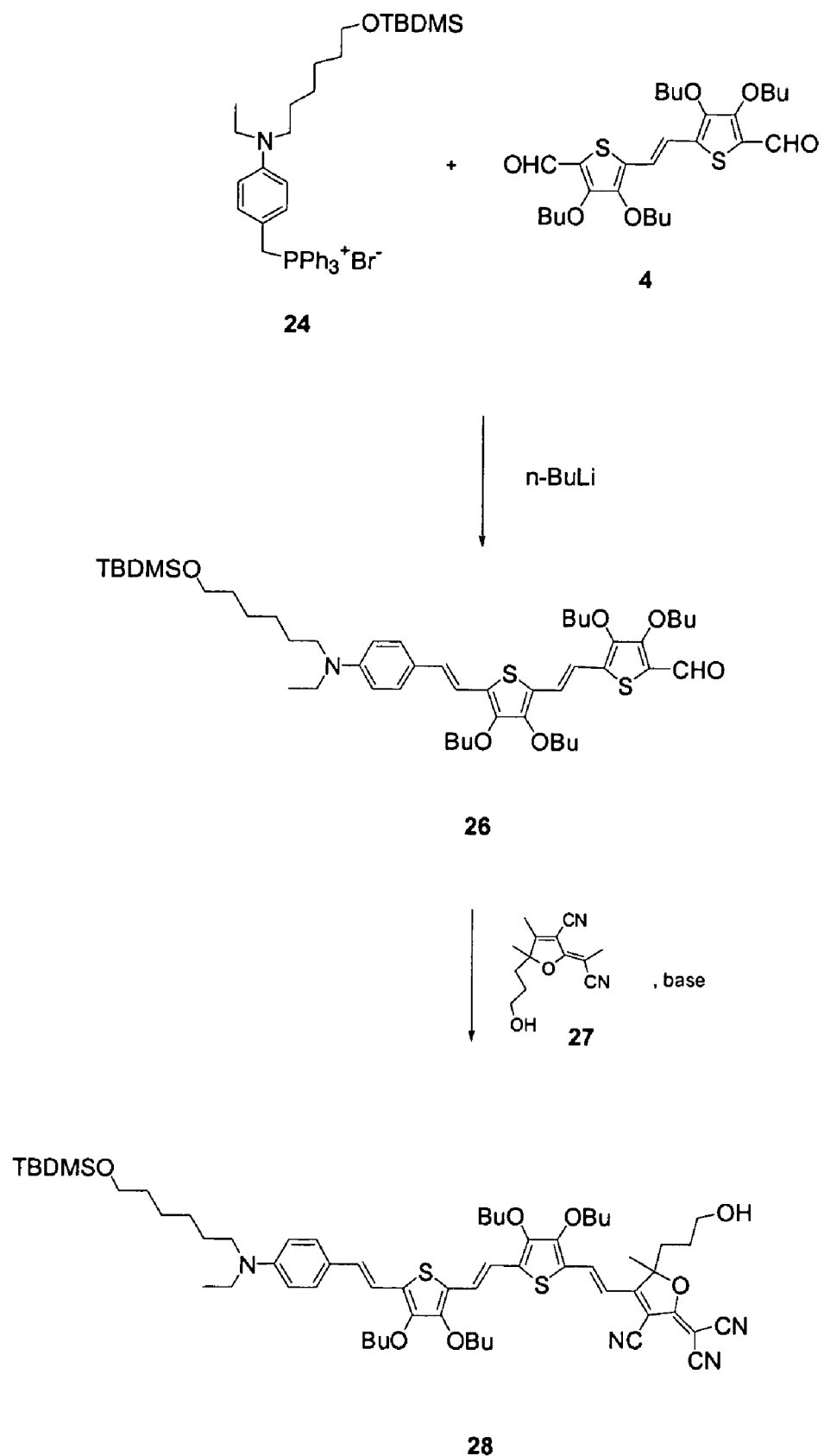
Figure 10:
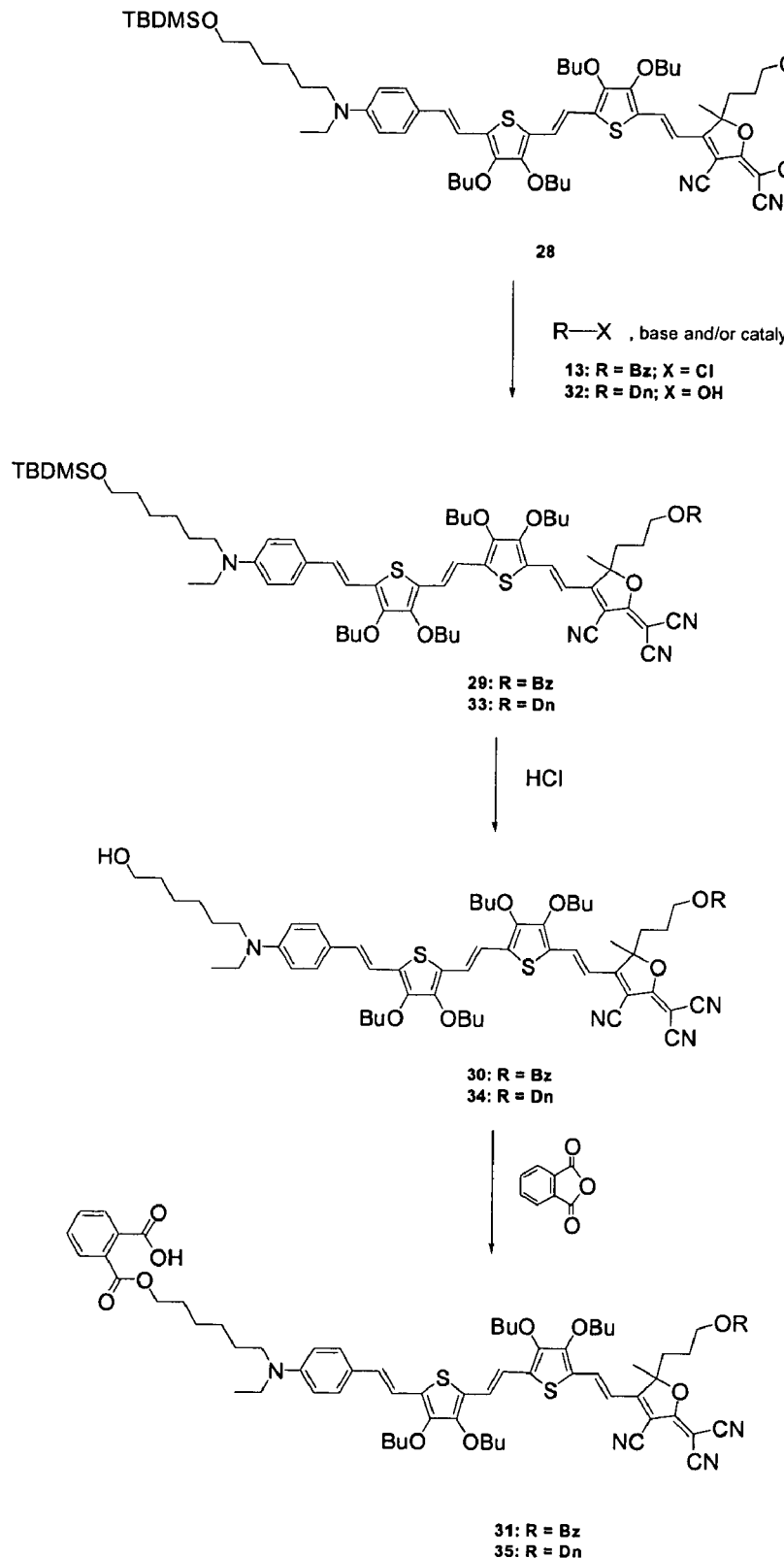
Figure 11:
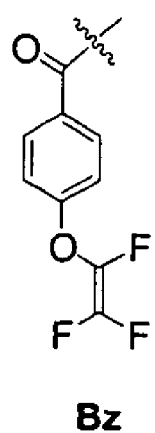
FIG. 11 illustrates two crosslinkable groups.
Figure 11:
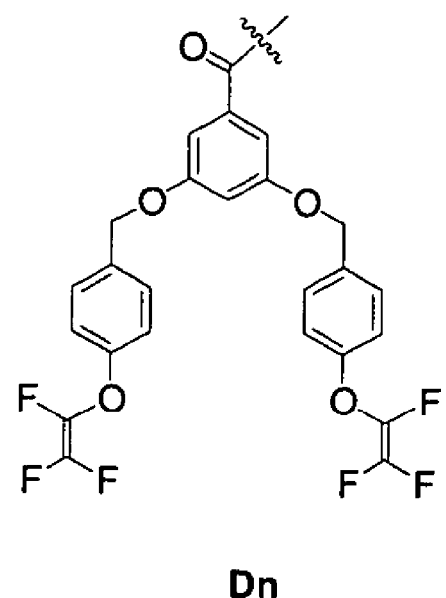
Figure 12:
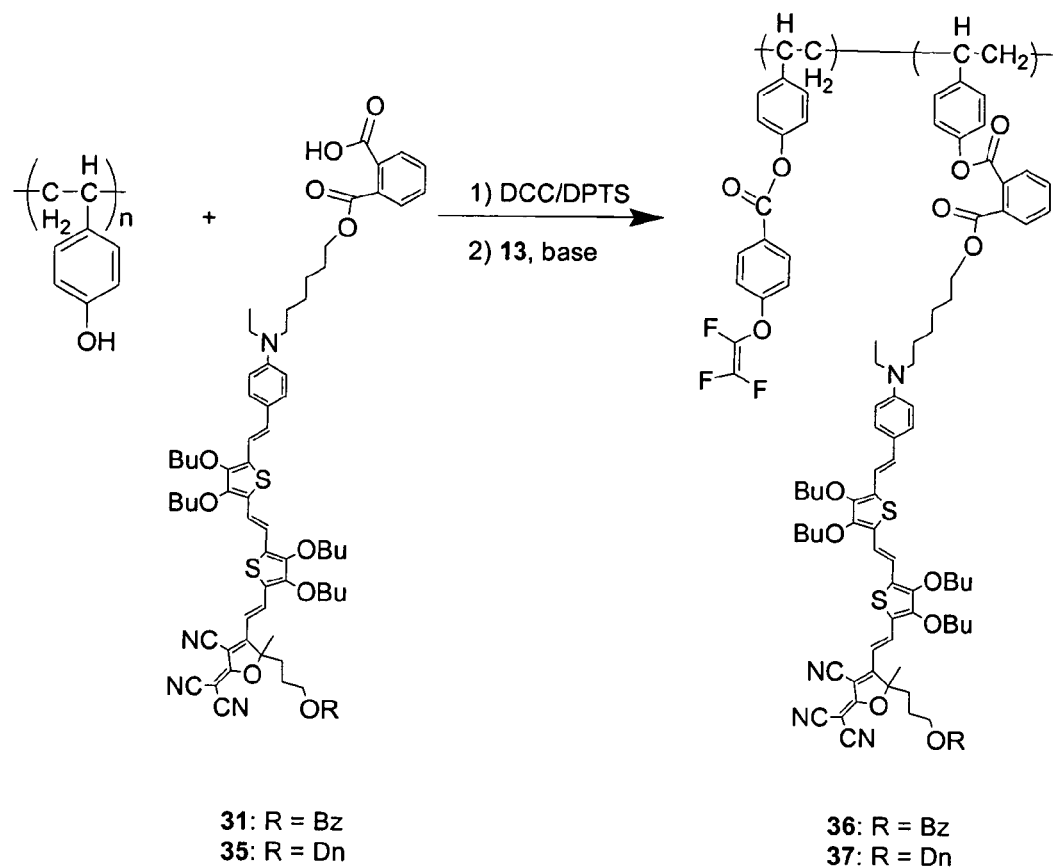
FIG. 12 outlines the syntheses of two side chain polymers with pendant nonlinear optical chromophores.

Referring to FIG. 7, a three-neck 500 ml flask equipped with a thermometer, a magnetic stirrer bar, and an addition funnel was charged with 25.3 g (0.1 mol) of Compound 15, which can be prepared as in *Macromolecules* 1996, 29(3), 852–860). The flask was purged with nitrogen before introducing 200 mL of dry ether and then was cooled in dry ice-acetone bath. 76 mL of 1.7 M t-BuLi in pentane was dropped into flask from addition funnel below −65° C. After completion of this addition, the reaction was kept in the above bath for 1 hour. 19.4 g of 2,3,4,5,6-pentafluorostyrene was then added and allowed to react for 1 h before removing the cooling bath and letting the temperature reach 0° C. At this moment, dilute HCl aqueous solution was poured into the flask to quench the reaction until the aqueous layer became acidic. The organic layer was separated, dried over $MgSO_4$, evaporated, and purified on a silica gel column with hexanes to give Compound 16 as a white solid (10.08 g, 29%).

A mixture of Compound 16, (1.7411 g, 5.0 mmol), THF (5 mL), and 2,2'-azoisobutyronitrile (AIBN) in a 25 mL flask equipped with a condenser was kept under nitrogen atmosphere at 76° C. for 5 hours and 60° C. overnight. The reaction was allowed to cool and the polymer was collected after precipitation by the addition of hexanes and filtration to give 1.2 g of Polymer 17 as a white powder.

The syntheses of the following compounds (Compounds 18–37) are described below with reference to FIGS. 8–12.

Compound 19: Compound 18 (prepared in a similar manner as the preparation of N-(6-hydroxyhexyl)-N-methylaniline in U.S. Pat. No. 5,395,556) (111 g, 0.5 mol) and acetic anhydride (76.5 g, 0.75 mol) were mixed and heated to 65° C. for 20 h. The reaction mixture was poured into water and extracted with $CH_2Cl_2$. The crude oil was purified by flash column with hexane/ethyl acetate (3:1). The product, 110 g, was obtained with 84% yield.

Compound 20: DMF (45.5 g, 0.624 mol) was placed in a three-neck flask. At 0° C., $POCl_3$ (76.3 g, 0.499 mol) was added dropwise. Compound 19 (109.5 g, 0.416 mol) was then added. It was stirred at room temperature for 30 min and heated at 100° C. for 3 h. The reaction mixture was then poured into water and neutralized with $NaHCO_3$. After extraction with $CH_2Cl_2$, the mixture was purified by flash column with hexane/ethyl acetate (5:2). The product, 96.2 g, was obtained with 80% yield.

Compound 21: Compound 20 (96 g, 0.33 mol) and 600 mL ethanol were mixed. $K_2CO_3$ (50 g, 0.36 mol) was added while stirring. The mixture was stirred at room temperature for 4 h. $CH_2Cl_2$ was added and it was dried over $MgSO_4$. After filtration and removing the solvent, it was purified by flash column with ethyl acetate/$CH_2Cl_2$ (3:2). The product, 54.3 g, was obtained with 66% yield.

Compound 22: Compound 21 (54 g, 0.217 mol), TBDMS-Cl (42.4 g, 0.282 mol), imidazole (38.3 g, 0.563 mol) and 140 mL DMF were mixed and heated at 50° C. for 10 h. The mixture was poured into water and extracted with $CH_2Cl_2$. Then it was purified with hexane/ethyl acetate (3:1). The product, 68.2 g, was obtained with 87% yield.

Compound 23: Compound 22 (68 g, 0.187 mol) was dissolved in 200 mL methanol. $NaBH_4$ was mixed with 7% NaOH solution (4 mL) and diluted with 30 mL water and then added dropwise into the above solution at 0° C. After stirred at room temperature for 3 h, it was poured into water and extracted with $CH_2Cl_2$. It was then purified by flash column with hexane/ethyl acetate (2:1). The product, 58 g, was obtained with 84% yield.

Compound 24: Compound 23 (57.5 g, 0.157 mol), $PPh_3 \cdot HBr$ (48.6 g, 0.142 mol) and 400 mL $CHCl_3$ were mixed and heated to reflux for 3 h with Dean-Stark set-up. The mixture was then condensed by removing most of the solvent and precipitated with diethyl ether. The product, 82 g, was obtained with 84% yield.

Compound 26: Compound 24 (71 g, 0.103 mol) was dissolved in 2000 mL THF. At −40° C., BuLi (45 mL, 0.113 mol) was added dropwise. It was stirred at room temperature for 30 min. The above solution was added dropwise into a solution of compound 4 (48 g, 0.09 mol) in 1400 mL THF. The reaction mixture was stirred for 10 h. After removing the solvent, it was purified by flash column with $CH_2Cl_2$/hexane/ethyl acetate (4:4:0.2). The product, 58.1 g, was obtained in 75% yield.

Compound 27: can be prepared as described below, or by the methods described in Liu, S; Haller, M. A.; Ma, H.; Dalton, L. R.; Jang, S. -H.; Jen, A. K. Y. *Adv. Mater.* 2003, 15 (7–8), 603–607.

Compound 28: Compound 26 (30 g, 34.5 mmol), compound 27 (10 g, 41.5 mmol), piperidene (catalytic amount) and 15 mL $CHCl_3$ were mixed and heated to reflux for 5 h. The reaction mixture was purified by flash column with hexane/ethyl acetate/$CH_2Cl_2$ (4:1.2:4). The product, 15.6 g, was obtained with 45% yield.

Compound 29: Compound 28 (7.13 g, 6.52 mmol) and pyridine (1.32 mL, 16.3 mmol) were dissolved in 80 mL $CH_2Cl_2$. Compound 13 (3.1 g, 13.04 mmol) in 10 mL $CH_2Cl_2$ was added dropwise at 0° C. The mixture was stirred at room temperature for 12 h and then poured into water. It was extracted with $CH_2Cl_2$ and purified by flash column with hexane/$CH_2Cl_2$/ethyl acetate (4:4:0.4). The product, 7.7 g, was obtained with 91% yield.

Compound 30: Compound 28 (7.6 g, 5.875 mmol) was dissolved in 150 mL THF. HCl solution (1N, 50 mL) was added. It was stirred at room temperature for 12 h and then neutralized with $NaHCO_3$ solution. After being extracted with $CH_2Cl_2$, it was purified by flash column with hexane/$CH_2CL_2$/ethyl acetate (1:2:1). The product, 5.7 g, was obtained in 82% yield.

Compound 31: Compound 30 (1 g, 0.848 mmol), DMAP (0.021 g, 0.017 mmol) and triethyl amine (0.24 mL, 1.7 mmol) were dissolved in 30 mL $CH_2Cl_2$. Phthalic anhydride (0.157 g, 1.06 mmol) was added and it was stirred at room temperature for 12 h. It was then washed with 1N HCl solution, extracted with $CH_2Cl_2$, and washed with $NaHCO_3$ solution and water. The mixture was purified by flash column with $CH_2Cl_2$/acetone (2.5:1). The product, 0.82 g, was obtained with 73% yield.

Compound 32 was prepared as described below. The synthesis is based on Luo, J.; Liu, S.; Haller, M.; Liu, L.; Ma, H.; Jen, A. K. Y. Adv. Mater. 2002, 14(23), 1763–1768).

Compound 33: Compound 28 (4.2 g, 3.84 mmol), compound 32 (2.63 g, 4.99 mmol) and DPTS (0.3 g, 1.01 mmol) were dissolved in 30 mL $CH_2Cl_2$. DCC (1.23 g, 5.95 mmol) was added and it was stirred at room temperature for 12 h. After filtration and removing the solvent, the mixture was purified by flash column with hexane/$CH_2Cl_2$/ethyl acetate (4:4:0.4). The product, 5.88 g, was obtained with 95.6% yield.

Compound 34: Compound 33 (5.85 g, 3.65 mmol) was dissolved in 100 mL THF. HCl solution (1N, 30 mL) was added and it was stirred at room temperature for 12 h. The mixture was then extracted with $CH_2Cl_2$ and washed with $NaHCO_3$ solution. It was purified by flash column with $CH_2Cl_2$/ethyl acetate (12:1). The product, 4.77 g, was obtained with 88% yield.

Compound 35: Compound 34 (3.5 g, 2.35 mmol), DMAP (0.057 g, 0.47 mmol) and triethyl amine (0.66 mL, 4.71 mmol) were dissolved in 70 mL $CH_2Cl_2$. Phthalic anhydride (0.44 g, 2.94 mmol) was added and it was stirred at room temperature for 12 h. It was then washed with 1N HCl solution, extracted with $CH_2Cl_2$, and washed with $NaHCO_3$ solution and water. The mixture was purified by flash column with $CH_2CL_2$/acetone (2.5:1). The product, 2.3 g, was obtained with 60% yield.

Polymer 36: (prepared in a similar manner to that described in Luo, J.; Liu, S.; Haller, M.; Liu, L.; Ma, H.; Jen, A. K. Y. Adv. Mater. 2002, 14(23), 1763–1768) Vacuum-dried poly(4-vinylphenol) (0.9436 g), DPTS (0.231 g, 0.786 mmol), and compound 31 (1.044 g) were dissolved into THF (30 ml) and $CH_2Cl_2$ (10 ml). After addition of DCC (0.404 g, 1.965 mmol), the solution was stirred at room temperature for 40 hrs. Then compound 13 (4.05 g, 17.12 mmol) and $N(i-Pr)_2Et$ (1.806 g, 14 mmol) were added. After an additional 24 hrs, the reaction mixture was evaporated to about 10 ml for precipitation in methanol. The solid collected by filtration was dissolved in $CH_2Cl_2$ for precipitation again. This precipitation was repeated 8 times. The polymer collected was dried under vacuum to give 2.43 g of polymer 36 as a dark blue powder.

Polymer 37: (prepared in a similar manner to that described in Luo, J.; Liu, S.; Haller, M.; Liu, L.; Ma, H.; Jen, A. K. Y. Adv. Mater. 2002, 14(23), 1763–1768) Compound 35 (1.0287 g), vacuum-dried poly(4-vinylphenol) (0.7555 g), and DPTS (0.1851 g, 0.6288 mmol), were dissolved into THF (30 ml). After addition of DCC (0.404 g, 1.965 mmol) and $CH_2Cl_2$ (10 ml), the solution was stirred at room temperature for 47 hrs. Then compound 13 (3.71 g, 15.7 mmol) and $N(i-Pr)_2$ Et (1.8 g, 14 mmol) were added. After an additional 2 days, the reaction mixture was evaporated to about 10 ml for precipitation in methanol. The solid collected by filtration was dissolved in $CH_2Cl_2$ for precipitation again. This precipitation was repeated 8 times. The polymer collected was dried under vacuum to give 2.04 g of black blue powders.

Compound 27 intermediates: To diisopropylethyl amine (18.48 g, 143 mmol) in 200 mL of dichloromethane was added 3-acetyl-1-propanol (13.28 g, 130 mmol) at 0° C. After the solution was stirred for 0.5 hour, chloromethylmethyl ether (13.08 g, 162.5 mmol) was added while the temperature was maintained at 0° C. The resulting solution was stirred for another 1 hour, brought to room temperature and stirred overnight. Organic solvent was removed via rotary evaporation. The residue was treated with 100 mL of brine and extracted with 3×150 mL of diethyl ether. The organic layers were combined, dried over $Na_2SO_4$ and concentrated via rotary evaporation. The crude product was purified via a flash chromatography with dichloromethane as eluent to afford 5-methoxymethoxy-2-pentanone (14.3 g, yield: 75) as a pale oil.

To a solution of ethyl vinyl ether (19.47 g, 270 mmol) in THF was added 106 mL of tert-butyl lithium (1.7 M, 180 mmol) dropwise at −78° C. The solution was warmed to 0° C. with an ice bath, stirred for another one hour and then re-cooled to −78° C. To this lithiated enol ether was added dropwise a solution of 5-methoxymethoxy-2-pentanone (13.16 g 90 mmol) in 10 mL of THF. The resulting mixture was stirred for one hour at −78° C. and one and a half hour at 0° C., and then slowly warmed up to room temperature. The reaction mixture was quenched with 70 mL of saturated $NH_4Cl$ aq. The organic layer was separated and the aqueous layer was extracted with 3×100 mL of diethyl ether. The combined organic layer was dried over $Na_2SO_4$ and concentrated via rotary evaporation to afford 2-ethoxy-3-hydroxy-6-methoxymethoxy-3-methyl-1-hexene in quantitative yield (19.4 g). The crude product was used in the subsequent reaction without further purification.

To a solution of 2-ethoxy-3-hydroxy-6-methoxymethoxy-3-methyl-1-hexene (8.99 g. 41.2 mmol) in 50 mL of methanol was added dropwise 1 M HCl (100 mL, 100 mmol) at room temperature. The exothermic reaction was cooled by water bath and monitored by TLC. After being stirred for two hours, the resulting mixture was neutralized with $NaHCO_3$, concentrated via rotary evaporation and extracted with 3×120 mL of dichloromethane. The combined organic layer was dried over $Na_2SO_4$ and concentrated. The crude product was purified by flash column chromatography using hexanes/ethyl acetate (2/1-1/1) as eluent to afford 4.6 g of 3-methyl-3-hydroxy-6-methoxymethoxy-2-hexanone (yield 59).

To a solution of 3-methyl-3-hydroxy-6-methoxymethoxy-2-hexanone 3 (6.66 g, 35 mmol), which was dried over MgSO$_4$ overnight prior to the reaction, and malononitrile (5.55 g, 84 mmol) in 100 mL of absolute ethanol was added methanol washed lithium (7.6 mg, 1.1 mmol). This solution was refluxed in a Soxhlet apparatus charged with 4 Å molecular sieve overnight. At the end, 1 mL of water was added to quench the reaction. Organic solvent was removed and the residue was purified via flash column chromatography using hexanes/ethyl acetate (3/1-1/1) as eluent to afford 2-dicyanomethylene-3-cyano-4,5-dimethyl-5-(3'-methoxymethoxypropyl)-2,5-dihydrofuran (3.7 g, 37 yield).

Compound 27: To a solution of 2-dicyanomethylene-3-cyano-4,5-dimethyl-5-(3'-methoxymethoxypropyl)-2,5-dihydrofuran 4 (2.5 g, 8.7 mmol) in 50 mL of THF was added dropwise 58 mL of 6M HCl (348 mmol) at room temperature. The solution was then heated to 65 °C. for 4 hours and then slowly poured into a solution of 72 g of K$_2$CO$_3$ in 87 mL of water on an ice bath. Organic solvent was removed via rotary evaporation and the remaining solution was extracted with 3×150 mL of diethyl ether. The combined organic layer was dried over Na$_2$SO4 and concentrated. The residue was purified using flash column chromatography with a gradient eluent (hexanes/ethyl acetate (1/1) and then pure ethyl acetate) to afford Compound 27 (1.5 g).

Compound 32 intermediates: To a solution of 4-(trifluorovinyloxy)-bromobenzene (9.25 g, 36.6 mmol) in dry diethyl ether (60 mL) at −78° C. was added t-BuLi (23.7 mL, 1.7 M in pentane) dropwise. One hour later, DMF (4.3 mL, 1.5 eq) was added dropwise. The reaction mixture was stirred at −78° C. for 1 h. Then the reaction mixture was allowed to warm up to room temperature for about 45 min, and quenched by adding water (10 mL). The ethereal layer was collected and the aqueous layer was extracted with diethyl ether. The combined organic layer was washed with water twice (50 mL×2), and dried over sodium sulfate. After filtration and evaporation of the solvent, the product was dried in vacuum overnight to give 4-(trifluorovinyloxy) benzaldehyde as yellow oil, which can be used in next step without further purification. $^1$H NMR (CDCl$_3$): δ 10.18 (s, 1H), 7.85 (d, J=8.8 Hz, 2H), 7.17 (d, J=8.8 Hz, 2H).

To a solution of 4-(trifluorovinyloxy)benzaldehyde (about 35 mmol) in benzene/ethanol (75/75 mL) at room temperature was added sodium borohydride (1.8 g, 1.3 eq). The resulting mixture was stirred at room temperature for 3 h. Under reduced pressure, all the solvent was evaporated. The residue was extracted by CH$_2$Cl$_2$ for 1 h and dried over sodium sulfate. The product was purified by chromatography using CH$_2$Cl$_2$ as the eluent to afford 4-(trifluorovinyloxy)benzyl alcohol as colorless oil (5.0 g, yield 68%). $^1$H NMR (CDCl$_3$): δ 7.36 (d, J=8.8 Hz, 2H), 7.09 (d, J=8.8 Hz, 2H), 4.67 (s, 2H), 2.03 (s, 1H).

To freshly distilled 2,2,2-trichloroethanol (25 mL) was added 3,5-dihydroxybenzoic acid 4.50 g, 29.2 mmol) followed by concentrated sulfuric acid (1.0 mL), and mixture was stirred vigorously and heated at 90° C. for 48 h under nitrogen. The reaction mixture was cooled and evaporated to dryness under reduced pressure. The crude product was purified by flash chromatography eluting with CH$_2$Cl$_2$ gradually increasing to 1:10 diethyl ether/CH$_2$Cl$_2$, to give (2,2,2-trichloroethyl) 3,5-dihydroxybenzoate as a viscous oil (5.12 g, yield 61.4%).

To a solution of compound (2,2,2-trichloroethyl) 3,5-dihydroxybenzoate (2.04 g, 7.14 mmol), 4-(trifluorovinyloxy)benzyl alcohol (3.2 g, 15.6 mmol), and triphenylphosphine (6.0 g, 22.9 mmol) in freshly distilled THF (40 mL) was added dropwise diethyl azocarboxylate (3.6 mL, 22.7 mmol). The reaction mixture was allowed to stir at room temperature overnight, and then all the solvent was evaporated under reduced pressure. The crude product was purified by column chromatography using CH$_2$Cl$_2$/hexane (1:3, v/v) as the eluent to afford (2,2,2-trichloroethyl) 3,5-di((4-trifluorovinyloxy)benzyloxy)benzoate as colorless oil (3.39 g, yield 72%).

Compound 32: To a solution of (2,2,2-trichloroethyl) 3,5-di((4-trifluorovinyloxy)benzyloxy)benzoate (3.38 g, 5.14 mmol) in a mixture of THF/acetic acid (10 mL/10 mL) was added 2.3 g of the zinc dust. The reaction mixture was allowed to stir vigorously under nitrogen for 3 h, and filtered. Most of the solvent was evaporated, and the residue of the filtration was redissolved in diethyl ether. The solution was washed by water (100 mL×3), and dried over sodium sulfate. The crude product was purified by column chromatography using CH$_2$Cl$_2$/acetone (2:1, v/v) as the eluent to afford 32 as white solid (2.60 g, yield 96%). $^1$H NMR (CDCl$_3$): δ 7.36 (d, J=8.8 Hz, 4H), 7.26 (d, J=2.6 Hz, 2H), 7.04 (d, J=8.8 Hz, 4H), 6.72 (t, J=2.6 Hz, 1H), 4.97 (s, 4H).

A crosslinked electro-optic polymer thin film including Compound 14 in Polymer 17 was prepared by: 1) preparing a solution of Compound 14 and Polymer 17 (15% by weight loading of Compound 14 with respect to Polymer 17) in cyclopentanone (30% by weight loading of Compound 14 and Polymer 17 (total solids) with respect to cyclopentanone); 2) spin depositing the solution at 500 rpm for 5 sec and 1300 rpm for 30 sec on a 2" ITO substrate; 3) corona poling the system at 180° C. and 4.5 kV for 10 min, 5.5 kV for 5 min, 6.5 kV for 5 min, and 7.5 kV for 5 min; and 4) allowing the crosslinked film to cool to room temperature under the 7.5 kV field.

A crosslinked electro-optic polymer film formed from Polymer 36 was prepared by spin coating a 25% (by weight) solution of Polymer 36 in cyclopentanone on an ITO covered glass slide. The solution was filtered through a 0.2 μm Nylon filter, spin coated at 500 rpm for 6 seconds and 1000 rpm for 30 seconds, and soft baked at 50° C. overnight under vacuum to give a 3.2 μm film. The film was Corona poled with a needle at 20 kV and heated to 220° C. for 5 min for crosslinking. The film was allowed to cool to room temperature under the applied field to give an electro-optic film with an $r_{33}$ of 36 pm/V at 1.31 μm.

Other embodiments are within the following claims.

What is claimed is:

1. A composition comprising a linear polymer, the linear polymer comprising pendant chromophores having the formula D-π-A, wherein π is a π bridge including a thiophene ring having oxygen atoms bonded directly to the 3 and 4 positions of the thiophene ring, D is a donor, and A is an acceptor.

2. The composition of claim 1, wherein the oxygen atoms are independently substituted with an alkyl, heteroalkyl, aryl, or heteroaryl group.

3. A composition comprising a linear polymer, the linear polymer comprising pendant chromophores having the formula:

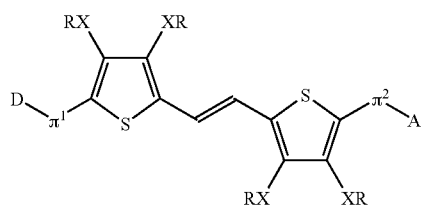

wherein, independently at each occurrence: π¹ is absent or a π-bridge; π² is absent or a π-bridge; D is an donor; A is an acceptor; X is O or S; and R is an alkyl, aryl, heteroalkyl, or heteroaryl group.
4. The composition of claim 3 wherein the donor is selected from the group consisting of:
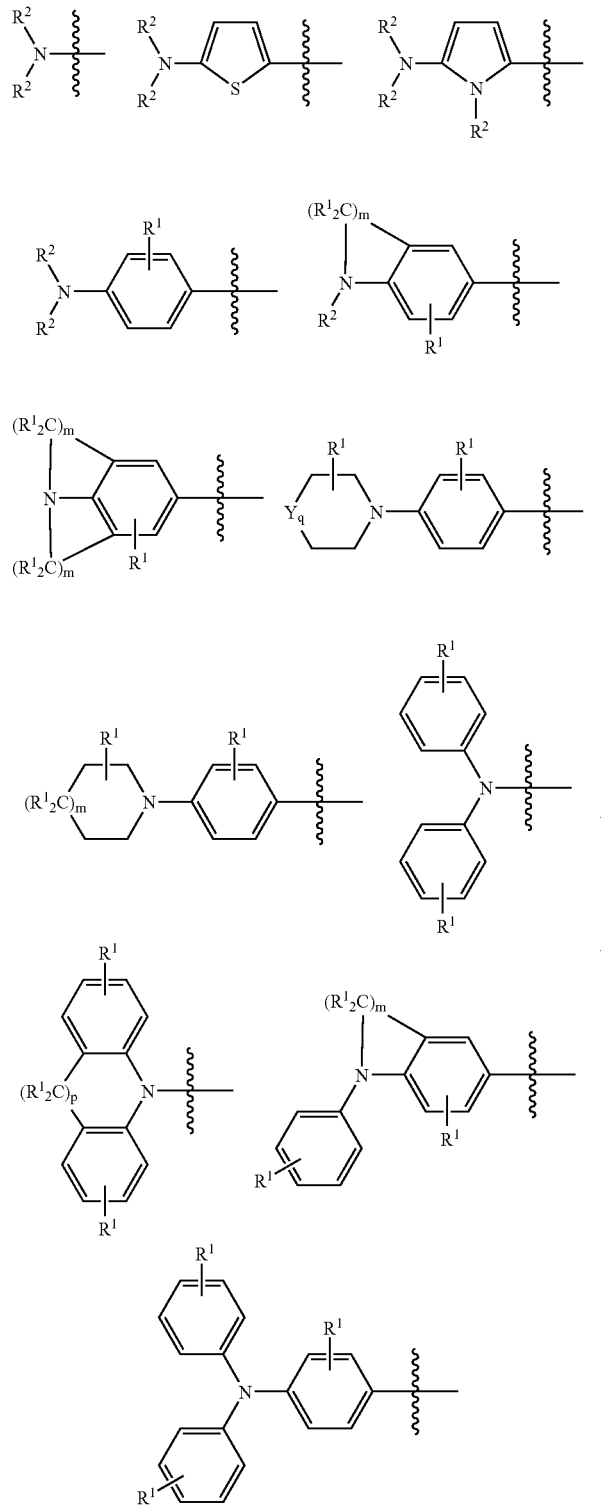
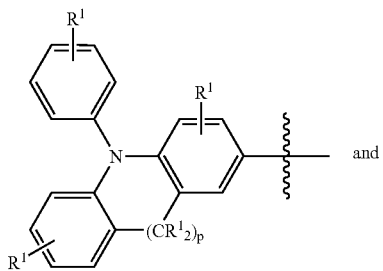
and
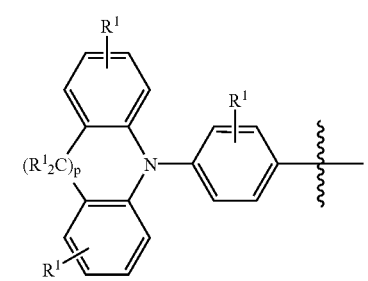
and the acceptor is selected from the group consisting of
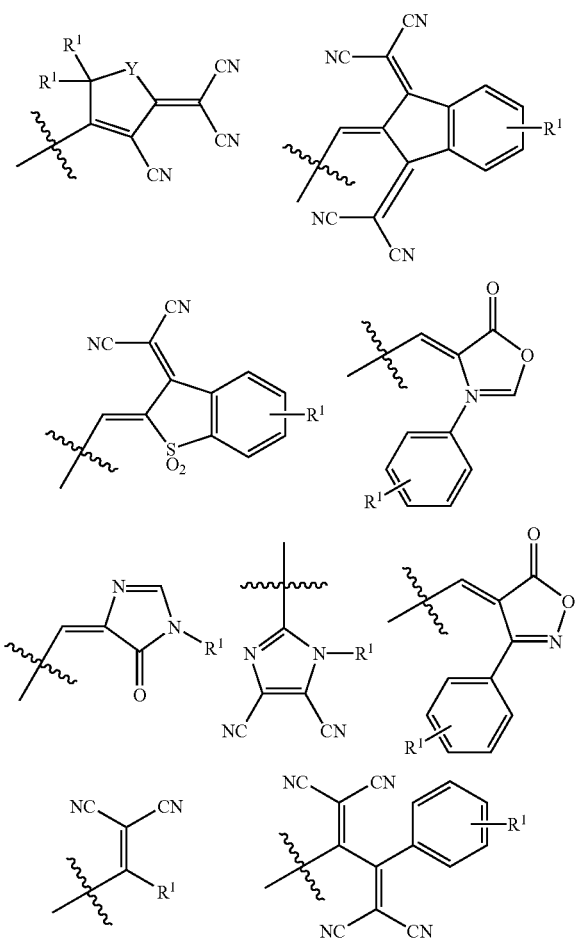

-continued

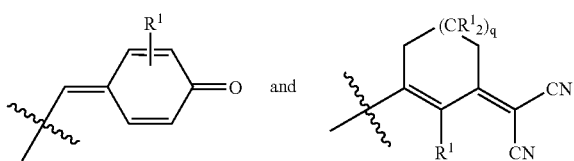

wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1.

5. The composition of claim 4, wherein the donor is selected from the group consisting of

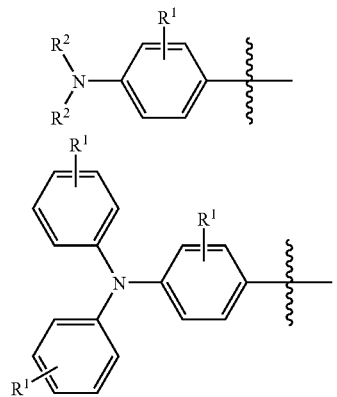

wherein, independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; and $R^2$ is hydrogen or an alkyl, aryl, heteroalkyl, or heteroaryl group.

6. The composition of claim 3, wherein each X is oxygen and each R group is an alkyl group.

7. The composition of claim 3, wherein the polymer further comprises pendant crosslinkable groups.

8. The composition of claim 7, wherein the chromophore further comprises at least one crosslinkable group.

9. An electro-optic device, comprising the composition of claim 1.

10. The electro-optic device of claim 9, wherein the electro-optic device is selected from the group consisting of an optical modulator, an optical switch, and an optical directional coupler.

11. The electro-optic device of claim 9, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end.

12. The electro-optic device of claim 9, comprising: 1) an input; 2) an output; 3) a first waveguide extending between the input and output; and 4) a second waveguide aligned to the first waveguide and positioned for evanescent coupling to the first waveguide.

13. An optical router including the electro-optic device of claim 9.

14. A communications system including at least one electro-optic device of claim 9.

15. A method of data transmission comprising transmitting light through the composition of claim 1.

16. A method of telecommunication comprising transmitting light through the composition of claim 1.

17. A method of transmitting light comprising directing light through or via the composition of claim 1.

18. A method of routing light through an optical system comprising transmitting light through or via the composition of claim 1.

19. A phased array radar system comprising the composition of claim 1.

* * * * *